(12) United States Patent
Myers et al.

(10) Patent No.: US 8,328,811 B2
(45) Date of Patent: Dec. 11, 2012

(54) MINIMALLY INVASIVE SURGICAL DRIVER

(75) Inventors: Reese K. Myers, Warsaw, IN (US); Andrew H. Berthusen, Warsaw, IN (US); Bryan Mendenhall, Claypool, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 741 days.

(21) Appl. No.: 12/165,914

(22) Filed: Jul. 1, 2008

(65) Prior Publication Data

US 2008/0275450 A1 Nov. 6, 2008

Related U.S. Application Data

(62) Division of application No. 11/238,354, filed on Sep. 29, 2005.

(51) Int. Cl.
*A61B 17/00* (2006.01)

(52) U.S. Cl. ........................................................ 606/79

(58) Field of Classification Search .............. 606/79–81; 285/306, 308, 317; 81/54, 57.42, 177.1, 81/177.6; 82/124; 30/276, 275, 381, 392, 30/394, 104–105

See application file for complete search history.

(56) References Cited

U.S. PATENT DOCUMENTS

| | | | | |
|---|---|---|---|---|
| 4,706,659 | A * | 11/1987 | Matthews et al. | 606/80 |
| 5,041,119 | A * | 8/1991 | Frigg et al. | 606/96 |
| 5,236,433 | A | 8/1993 | Salyer | |
| 5,387,216 | A * | 2/1995 | Thornhill et al. | 606/88 |
| 5,468,243 | A * | 11/1995 | Halpern | 606/80 |
| 5,643,271 | A * | 7/1997 | Sederholm et al. | 606/80 |
| 5,851,208 | A * | 12/1998 | Trott | 606/80 |
| 5,908,423 | A * | 6/1999 | Kashuba et al. | 606/80 |
| 5,957,925 | A * | 9/1999 | Cook et al. | 606/87 |
| 5,980,170 | A | 11/1999 | Salyer | |
| 6,053,922 | A | 4/2000 | Krause et al. | |
| 6,949,101 | B2 * | 9/2005 | McCleary et al. | 606/80 |
| 7,090,677 | B2 * | 8/2006 | Fallin et al. | 606/80 |
| 7,758,581 | B2 * | 7/2010 | Chervitz et al. | 606/80 |
| 2003/0187449 | A1 * | 10/2003 | McCleary et al. | 606/80 |
| 2004/0030344 | A1 | 2/2004 | Dye et al. | |
| 2004/0087958 | A1 | 5/2004 | Myers et al. | |
| 2004/0172036 | A1 | 9/2004 | Dye | |
| 2005/0038443 | A1 * | 2/2005 | Hedley et al. | 606/91 |
| 2005/0057042 | A1 * | 3/2005 | Wicks | 285/305 |
| 2005/0131414 | A1 * | 6/2005 | Chana | 606/80 |
| 2005/0216022 | A1 * | 9/2005 | Lechot et al. | 606/81 |
| 2005/0240192 | A1 * | 10/2005 | Lechot et al. | 606/80 |
| 2006/0074425 | A1 * | 4/2006 | Sutterlin et al. | 606/79 |
| 2009/0076511 | A1 * | 3/2009 | Osman | 606/80 |

* cited by examiner

*Primary Examiner* — Alvin Stewart
*Assistant Examiner* — Mary Hoffman
(74) *Attorney, Agent, or Firm* — Taylor IP, P.C.

(57) ABSTRACT

A method of removing bone material including the steps of drivingly connecting a bone removal tool to an output shaft; and rotating a plurality of drive shafts in an open frame, one of the plurality of drive shafts being connected to the output shaft.

20 Claims, 2 Drawing Sheets

MINIMALLY INVASIVE SURGICAL DRIVER

CROSS REFERENCE TO RELATED APPLICATIONS

This is a division of U.S. patent application Ser. No. 11/238,354, entitled "MINIMALLY INVASIVE SURGICAL DRIVER", filed Sep. 29, 2005, which is incorporated herein by reference.

BACKGROUND OF THE INVENTION

1. Field of the Invention

The present invention pertains generally to surgical instruments and, more particularly, to surgical instruments such as surgical tool drivers suited for use in orthopeadic surgical procedures.

2. Description of the Related Art

An orthopeadic driver assembly can be used to ream or cut a bone and thereby form the bone into a predetermined shape for receiving an orthopeadic implant. For example, an orthopeadic reamer assembly may be used to shape the interior or exterior surface of a bone. A rotary tool provides the rotational force and is connected to the driver, which is connected to the reamer. The driver generally has a shaft end and a drive end. The reamer may have a typically hemispherical shape and be attached to the drive end of the driver at the base of the hemisphere. The face of the reamer has a shape, which corresponds to the shape of an orthopeadic implant to be received within the bone, and includes a plurality of cutting teeth extending from the distal face. The reamer is positioned, oriented and placed against the bone surface to be cut, such as an acetabulum or glenoid and is plunge cut into the bone. The use of the reamer in this manner effectively removes a portion of the bone so that the bone is shaped to receive the implant.

Minimally invasive surgery reduces the size of the incision site so as to reduce trauma to the patient leading to reduced recovery time. Orthopeadic reamers have been designed for minimally invasive surgery, such as U.S. patent application Ser. No. 10/659,812, assigned to the assignee of the present invention. There are known orthopeadic drivers, which have flexible shafts. Flexible shafts allow the reamer to travel along a path in a non-linear manner resulting in a less than desirable opening in the bone.

What is needed in the art is a driver shaped for use in a minimally invasive surgical application that is cost effective to manufacture and maintain.

SUMMARY OF THE INVENTION

The present invention provides a driver that holds a drive head in a fixed position with the drive train being routed in a manner non-axial with the drive head.

The invention comprises, in one form thereof, a surgical driver including an open frame and a plurality of drive shafts rotationally routed in the open frame.

An advantage of the present invention is that the open frame allows for easy maintenance and cleaning of the driver.

Another advantage of the present invention is that it is easily disassembled for cleaning.

Yet another advantage of the present invention is that the removable input shaft readily mates with the drive shaft that is pinned to other link members.

Still another advantage of the present invention is that the axis of the output shaft is offset from the input axis of the driver.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrate one embodiment of the invention, in one form, and such exemplification is not to be construed as limiting the scope of the invention in any manner.

DETAILED DESCRIPTION OF THE INVENTION

Figure 1:
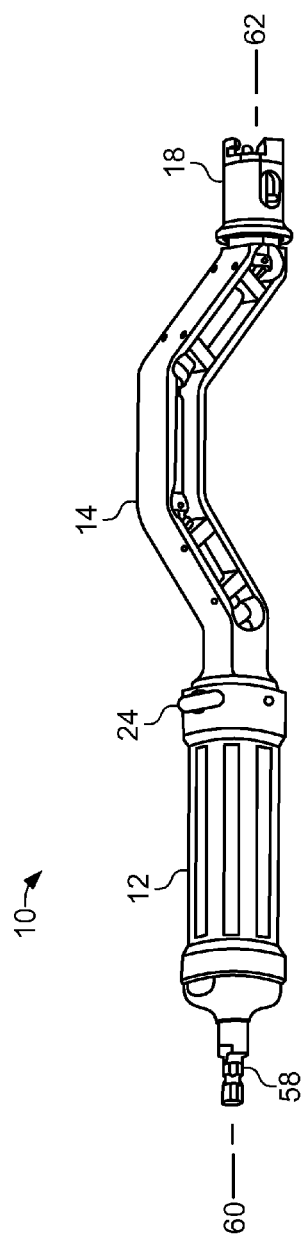
FIG. 1 is a perspective view of an embodiment of a minimally invasive surgical driver of the present invention.
Figure 2:
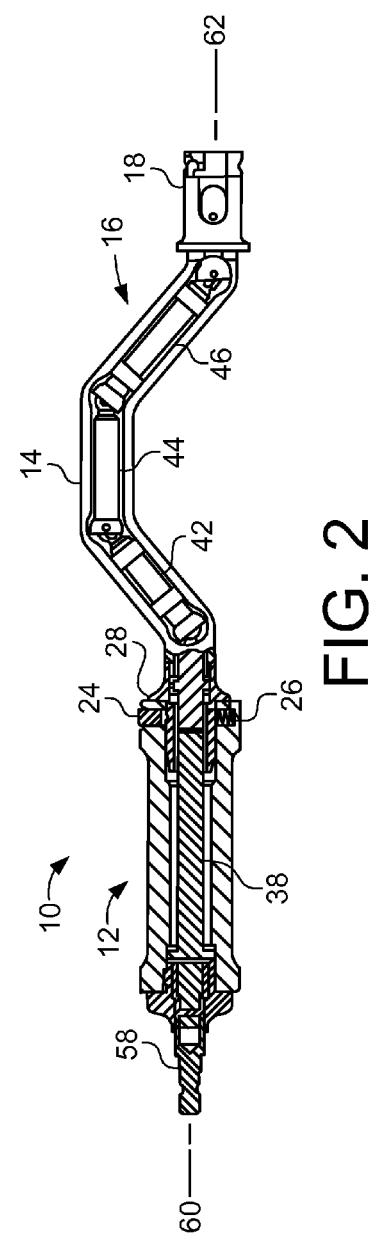
FIG. 2 is a side view of the driver of FIG. 1.
Figure 3:
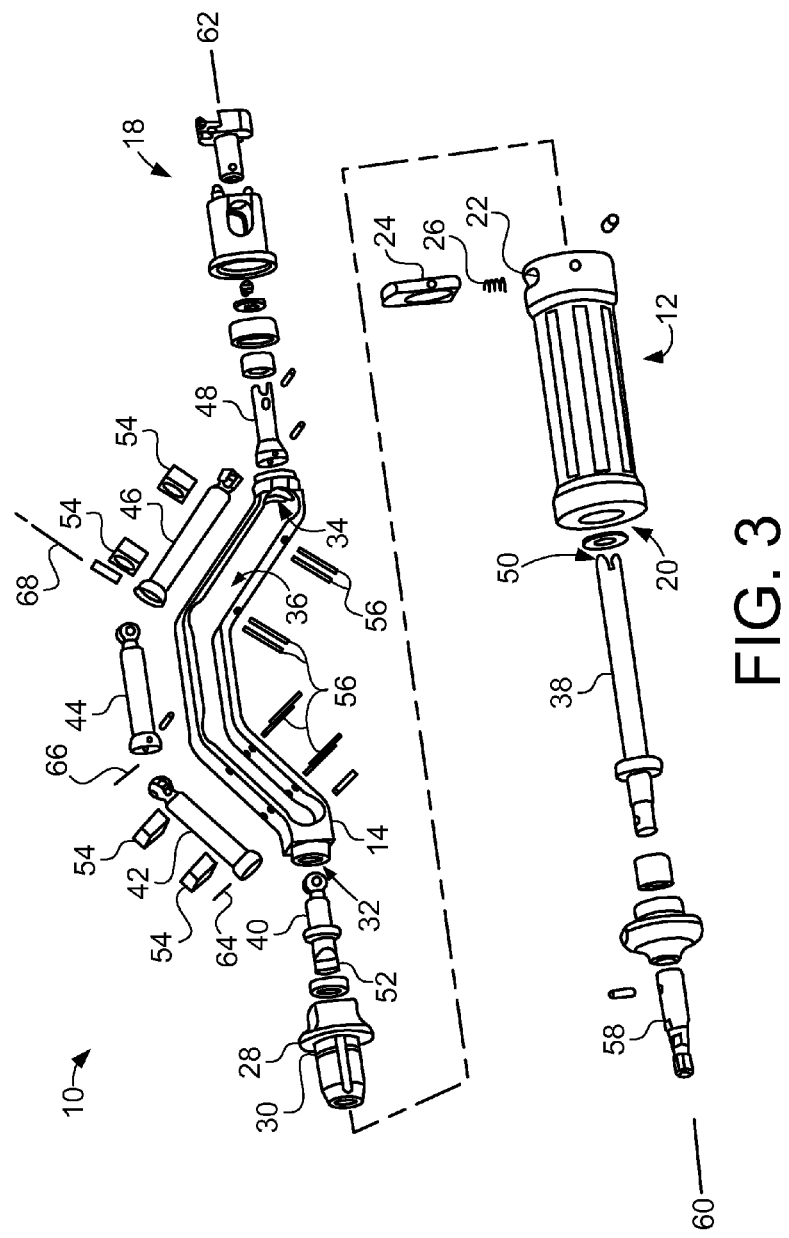
FIG. 3 is an exploded of the driver of FIGS. 1 and 2.

Referring now to the drawings, and, more particularly to FIGS. 1-3, there is shown an embodiment of a surgical driver assembly 10, which includes a handle assembly 12, a drive body 14, a drive train assembly 16 and a drive head 18. Handle assembly 12 includes an axial opening 20 and a radial opening 22 in which a pushbutton 24 and biasing device 26 is associated. A transition collar 28 interfaces with a portion of frame 14 and an end of handle 12 to secure frame 14 to handle 12. Transition collar 28 includes a groove 30, which interfaces with pushbutton 24 such that handle assembly 12 is connected to the rest of driver assembly 10 until pushbutton 24 is depressed against biasing device 26, thereby moving a feature in pushbutton 24 away from groove 30 allowing handle 12 to be removed from transition collar 28. This allows for quick disassembly of driver assembly 10 so that individual items may be maintained and/or cleaned.

Drive body 14, also known as an open frame 14 includes end openings 32 and 34 through which drive shafts are positioned in order to rotatably drive, drive head 18. Open frame 14 also includes a side opening 36, which is substantially the full length of frame 14. Side opening 36 extends completely through frame 14 and openings 32 and 34 open thereinto.

Drive train assembly 16 includes six drive shafts, and more particularly an input shaft 38, a drive shaft 40, a drive shaft 42, a drive shaft 44, a drive shaft 46, and an output shaft 48. Input shaft 38 traverses axial opening 20 of handle assembly 12 and either has a drive end formed on one end of shaft 38 or interfaces with a drive end 58. Another end of input shaft 16 includes slots 50, which are shown as two slots with angled portions which are formed to direct a blade 52 on drive shaft 40 into one of slots 50. The angled feature of slots 50 advantageously allow input shaft 38 to be inserted without the need of orienting shaft 38 since shaft 38 will self-align as it encounters blade 52, thereby positioning blade 52 in one of slots 50. As would be understood by those in the art, the features described on shafts 38 and 40 could be reversed to achieve the same function. Shafts 40, 42, 44, 46 and 48 each have a constrained substantially spherical element having a hole therethrough in order to facilitate a connection between each of shafts 40-48 by way of pins 56. A pin 56 is inserted through one end of each of shafts 42-48 to rotatably fix each respective shaft to a previous shaft. Prior to inserting pins 56, shafts 42 and 46 are inserted into blocks 54 and blocks 54 are positioned and pinned into place in open frame 14. Shaft 44 is constrained by the relative end positions of shafts 42 and 46 and is not otherwise constrained with any blocks such as blocks 54. As can be seen in FIG. 2, shaft 44 is only constrained in the position shown by being connected to shafts 42 and 46. Further, in FIG. 3 it can be more specifically seen that the constraint of shaft 44 to shaft 42 is by way of a pin inserted along axis 66, and shaft 44 is constrained to shaft 46 by way of another pin inserted along axis 68. Output shaft 48 is pinned to drive shaft 46 at one end thereof. Another end of output shaft 48 interface features that are formed therein to engage drive head 18 in order to allow a transfer of rotational movement from input shaft 38 through output shaft 48. Output shaft 48 is connected to a tool such as a bit or reamer for the removal of bone.

Input shaft 38 rotates about a rotational axis 60 and is driven by a rotational power tool, not shown. At an opposite end of drive assembly 10 output shaft 48 rotates about a rotational axis 62 with axes 60 and 62 being offset from each other and generally parallel to each other. The offset of rotational axis 62 from rotational axis 60 occurs because the length of drive shaft 46 is different than the length of drive shaft 42 with the angles of frame 14 being substantially complimentary. The longer length of drive shaft 46 causes rotational axis 62 to be offset from rotational axis 60.

Another feature of the present invention includes the positioning of pins 56 relative to each other. Shafts 40-48 are aligned such that pins 56, which connect shafts 40-48 together are not aligned. For example, shafts 42 and 44 have a pin 56 oriented along an interconnect axis 64 and shafts 44 and 46 are connected along an interconnect axis 66. Likewise, shafts 46 and 48 are interconnected along an interconnect axis 68. Interconnect axis 64 and interconnect axis 66 are shown here as being offset rotationally by 90° from one end of shaft 44 to the other end of shaft 44. In a rotational sense interconnect axis 68 is shown as being substantially parallel to interconnect axis 64. While this is shown in this manner it can also be understood that each of the interconnect axis 64-68 and any others within drive train 16 may be all offset from each other. It has been known that interconnections such as those between adjacent shafts will sometimes exhibit a phenomenon in which there is a non-uniform rotation with a slight acceleration and deceleration at certain points in the rotation of the shafts. By offsetting the interconnect axis the present invention advantageously reduces any amplification that may exist if interconnect axis were aligned.

Advantageously the present invention is shaped to allow its use in minimally invasive surgery techniques. Additionally, the open access of the drive shafts allows for ease of maintenance and cleaning of the individual parts. Additionally, the present invention allows for easy disassembly of the unit and includes features of self-alignment when the unit is reassembled. Further, interconnections are offset to minimize any surges in radial velocity caused by the linkages. Yet a further advantage of the present invention is that the input and output rotational axis are offset and substantially parallel to each other, thereby allowing the surgeon to take advantage of an offset in the rotational axis during the operational procedure.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of removing bone material, comprising the steps of:

drivingly connecting a bone removal tool to an output shaft; and rotating a plurality of drive shafts in an open frame, said plurality of drive shafts include a first drive shaft, a second drive shaft, and a third drive shaft, said first drive shaft having a plurality of constraints apart from any driving connections with other drive shafts, said second drive shaft not having any constraints in contact with said second drive shaft other than driving connections with said first drive shaft and said third drive shaft, said third drive shaft being connected to said output shaft.

2. The method of claim 1, wherein said open frame includes a side opening substantially along a length of said open frame, said open frame having two end openings that communicate with said side opening.

3. The method of claim 2, further comprising the step of removably connecting a handle to an end of said open frame.

4. The method of claim 3, wherein said handle is released from said frame by depressing a pushbutton.

5. The method of claim 1, further comprising the step of drivingly connecting a self-aligning input shaft to one of said plurality of drive shafts.

6. The method of claim 5, wherein said self-aligning input shaft includes one of an angled slot and a blade proximate an end of said self-aligning input shaft.

7. The method of claim 1, wherein said first drive shaft is longer than said second drive shaft.

8. The method of claim 1, wherein said plurality of drive shafts are in driving communication with an input shaft rotatable about a first axis, said output shaft being driven about a second axis, said first axis being offset from and substantially parallel to said second axis.

9. The method of claim 1, further comprising the step of removably connecting a handle with an opening therethrough to said open frame.

10. The method of claim 9, wherein said handle includes a pushbutton assembly that releases said handle from said open frame.

11. The method of claim 10, wherein an input shaft is retained in said handle until being released by depressing said pushbutton assembly.

12. A method of removing bone material, comprising the steps of:

drivingly connecting a bone removal tool to an output shaft; and rotating a plurality of drive shafts in an open frame, said plurality of drive shafts include a first drive shaft, a second drive shaft, and a third drive shaft, said first drive shaft having a plurality of constraints apart from any driving connections with other drive shafts, said second drive shaft not having any connections in contact with said second drive shaft other than driving connections with said first drive shaft and said third drive shaft, said third drive shaft being connected to said output shaft.

13. The method of claim 12, wherein said open frame includes a side opening substantially along the length of said open frame, said open frame having two end openings that communicate with said side opening.

14. The method of claim 13, further comprising the step of removably connecting a handle to an end of said open frame.

15. The method of claim 14, wherein said handle is released from said frame by depressing a pushbutton.

16. The method of claim 12, further comprising the step of drivingly connecting a self-aligning input shaft to one of said plurality of drive shafts.

17. The method of claim 16, wherein said self-aligning input shaft includes one of an angled slot and a blade proximate an end of said self-aligning input shaft.

18. The method of claim 12, wherein said first drive shaft is longer than said second drive shaft.

19. The method of claim 12, wherein said plurality of drive shafts are in driving communication with an input shaft rotatable about a first axis, said output shaft being driven about a second axis, said first axis being offset from and substantially parallel to said second axis.

20. The method of claim 12, further comprising the step of removably connecting a handle with an opening therethrough to said open frame.

\* \* \* \* \*